(12) United States Patent
Nowak et al.

(10) Patent No.: US 7,223,532 B1
(45) Date of Patent: May 29, 2007

(54) BLOOD COMPATIBLE POLYMER SURFACES

(75) Inventors: Gotz Nowak, Erfurt (DE); Elke Bucha, Erfurt (DE)

(73) Assignee: HaemoSys GmbH, Jena ( * ) Notice: Subject to any disclaimer, the term of this patent is extended or adjusted under 35 U.S.C. 154(b) by 472 days.

(21) Appl. No.: 10/130,616

(22) PCT Filed: Nov. 14, 2000

(86) PCT No.: PCT/EP00/11253

§ 371 (c)(1),
(2), (4) Date: Jan. 28, 2003

(87) PCT Pub. No.: WO01/36613

PCT Pub. Date: May 25, 2001

(30) Foreign Application Priority Data

Nov. 17, 1999 (DE) ............................... 199 55 341

(51) Int. Cl.
*A01N 1/02* (2006.01)
*A61F 2/00* (2006.01)
*C12Q 1/00* (2006.01)
*C12N 11/08* (2006.01)
*C12M 1/00* (2006.01)

(52) U.S. Cl. .............................. 435/2; 424/423; 435/4; 435/180; 435/283.1

(58) Field of Classification Search ..................... None
See application file for complete search history.

(56) References Cited

U.S. PATENT DOCUMENTS

| 4,664,669 A | * | 5/1987 | Ohyabu et al. | .......... | 428/304.4 |
| 5,906,744 A | * | 5/1999 | Carroll et al. | ............... | 210/516 |
| 6,929,955 B2 | * | 8/2005 | Bucha et al. | ................ | 436/531 |

FOREIGN PATENT DOCUMENTS

WO  WO 98/46648  * 10/1998

* cited by examiner

*Primary Examiner*—David M. Naff
(74) *Attorney, Agent, or Firm*—Kagan Binder, PLLC

(57) ABSTRACT

The invention relates to a blood-compatible surface comprising a polymer surface and a plurality of conjugates made of linkers and active agents immobilized thereon. The polymer surface contains similar or different structural units that carry carbonyl groups. The linkers contain a structural element that is able to form a hydrogen bridge bond. A polyorganosiloxane acting as the active agent is linked to the linkers.

19 Claims, 2 Drawing Sheets

BLOOD COMPATIBLE POLYMER SURFACES

This application is a 371 of PCT/EP00/11253 filed Nov. 14, 2000.

In the medical field plastic materials are used in a variety of applications. The exploration of interactions between plastic surfaces and living cells as well as of the improvement of the biocompatibility of such surfaces has been the subject-matter of intense research for more than 30 years. However, up to now, no solution has been found to design polymeric surfaces such that blood and blood constituents do not bind thereto. This applies particularly to highly active blood cells, such as blood platelets, which may lead to activation processes, particularly to blood coagulation, after attachment to the plastic surface.

By changing the charges on the surface, by forming microdomain structures as well as by introducing new polymer mixtures and copolymers some progress has been achieved in this field. Nevertheless no breakthrough could be achieved in the provision of the necessary blood- and protein-inert surfaces.

To achieve this goal, the present invention uses an interaction system disclosed in WO 98/46648, which allows the binding of for example bioactive substances to suitable plastic surfaces by means of specific linkers. By using inhibitors of thrombocyte or cell activation, which were immobilised on polymer materials employing these linkers, important prerequisites for providing such blood and protein compatible boundary layers could be made. According to the invention it could be shown that particularly polysiloxanes are present as activation inhibitors for this application. By applying these materials to plastic surfaces, blood constituents, particularly proteins, are prevented from forming deposits. It is known that silicone polymers impart increased blood compatibility to glass surfaces by applying them thereto. Attempts to fix the used silicone oils in active form on plastic surfaces however have not been successful so far.

Functional polymeric surfaces that allow the forming of the boundary layers according to the invention are also described in WO 98/46648. Homo or copolymers are used, the production of which requires at least a monomer type which contains, apart from a polymerisable double-bond or a polycondensable functional group, a further carbonyl group in the form of a ketone or a derivative of a carboxylic acid which does not take part in the polymerisation reaction. The polymer contains preferably a structural element of the formula (A):

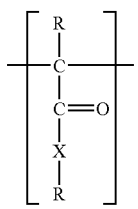

wherein groups R may be the same or different and represent an alkyl or aryl group or a hydrogen atom. The alkyl group can be linear or branched and consists preferably of 1 to 20 carbon atoms. The aryl group consists preferably of 6 to 18, more preferably of 6 to 12 carbon atoms. Group X is optional and represents O, N or $CH_2$. In case X=N, X has a further group R in addition to the one indicated in formula (A), which is independent of the other groups R as defined above.

A straight or branched, optionally substituted $C_{1-8}$-alkyl group, for example a methyl, ethyl or propyl group, is particularly preferred as alkyl group. Examples for substituents optionally present comprise one or more halogen atoms, for example fluorine, chlorine, bromine or iodine atoms or hydroxyl groups, $C_{1-6}$-alkyl groups or $C_{1-6}$-alkoxy groups or $C_{1-6}$-alkylthio groups. The aryl group is particularly preferably a monocyclic or bicyclic, optionally substituted aryl group, which may optionally comprise one or more heteroatoms. Examples of such aryl groups are phenyl groups, 1- or 2-naphthyl groups, indenyl or isoindenyl groups. Examples for heteroatom-containing aryl groups are $C_{3-9}$-heteroaryl groups, which contain heteroatoms selected from oxygen, sulphur or nitrogen atoms. Monocyclic heteroaryl groups comprise for example pyrolyl, furyl, thienyl, imidazolyl, N-methylimidazolyl, N-ethylimidazolyl, benzothiazolyl, quinazolinyl, naphthylpyridinyl, quinolyinyl, isoquinolinyl and tetrazolyl groups.

A preferred polymer which may be used in the present invention is a polyalkyl methacrylate (PAMA) having a alkyl group preferably comprising 1-6 C-atoms, such as polymethyl methacrylate (PMMA), polyethyl methacrylate (PEMA) or polypropyl methacrylate. Furthermore, polyvinyl acetate, polycyclohexyl methacrylates or polyphenylmethacrylate may be used. Polymethyl methacrylate is however particularly preferably provided with the inventive blood inert boundary layer.

Copolymers or polymer mixtures of optional amounts of the above-mentioned polymers with one another or with one or more additional polymer component(s), for example polystyrene, polyacrylnitrile or polyamides may be used as well. The amount of the monomers or structural units comprising a carbonyl group, preferably a structural element (A), in such mixtures or in such copolymers is preferably at least 20%, more preferably at least 40% and most preferably at least 60%.

The form of the used surface is, as described in WO 98/46648, in no way limited; e.g. plane structures, hollow articles as well as microparticles and capillary structures may be used. Microporous plastic surfaces which facilitate the bonding of the linker-active substance conjugates are preferably used. When used in the medical field, it is of course important to take into account the physiological acceptability of the used plastic.

Numerous objects and instruments used in the medical field are produced from the mentioned polymers and may thus be provided in blood compatible form after the application of the boundary layer disclosed herein. The range of products which may be used comprises plastic particles, blood tube systems, catheter materials, dialysers or membranes thereof, as well as stent- and implantation materials, which are relevant to replacement surgery. In addition to devices which are subjected to blood circulation within or outside the body, surfaces which get into contact with blood samples or which are used in subsequent treatments of such samples (e.g. sample containers, stirring devices) may advantageously be coated as well. Products and materials may be coated with a blood-inert boundary layer directly before they are used or already immediately after they have been produced.

Linkers, which may be used in the present invention for the immobilisation of activation or aggregation inhibitors, are molecules comprising at least two functional groups L1 and L2, which may be the same or different. One of these functional groups (L1) has to be capable of forming hydrogen bonds and thus allow the bonding of the linker to the polymer surface, which does not exclude that other subunits of the linker having a suitable electronical or spatial structure may also participate in this bonding. The functional group L2 is selected in such a way that a bond between the linker and the active substance can be effected. In order to be able to immobilise different active substances simultaneously on the polymer surface, the simultaneous use of several linkers with different groups L2 is possible. It is however also possible to use linkers of one type comprising two or more groups L2, which are the same or different. Linkers comprising several same or different groups L1 may be used as well. Preferably, L1 and L2 are linked by a branched or straight alkyl chain, which is interrupted by heteroatoms, preferably by hydrogen atoms.

Structural element L1 is preferably a polar hydrogen atom, as it is for example present in OH, SH, NH or PH bonds. The used linkers preferably have a hydroxyl group as structural element L1. The structural element is preferably located at a sufficiently water-soluble compound as linker. More preferably, L1 is attached to the linker in terminal position.

The functional group, by means of which an active substance may be, preferably covalently, linked to the linker (L2) is for example a hydroxyl or carboxyl group, a succinimidyl succinate, succinimydyl propionate, nitrophenyl carbonate, trisylate, epoxide, aldehyde, isocyanate or a maleimide. Further functional groups L2, by means of which linkers may be modified or activated for the immobilisation of a bioactive substance, are for example described in the catalogue of the company Shearwater Polymers, Inc., 2307 Spring Branch Rd., Huntsville, Ala. 35801 (USA).

In contrast to e.g. enzymes as bioactive substances, the polyorganosiloxanes used in the present invention to obtain blood compatibility are comparatively stable. They may be covalently linked to linkers having simple terminal functional groups, such as polyalkylene glycols, without their previous activation. Preferably, an ether or ester bond is present after linking the linker to the bioactive substance between the two components.

Polyalkylene glycols, polyalkylene imines, polyalkylene amines or polyalkylene sulfides, as well as polyoxacillines are preferably used as linkers, polyalkylene glycols being particularly preferred. The average polymerisation degree of such compounds is preferably below 50, more preferably below 30. The lower limit is generally 10, preferably 20, whereby the preferred polymerisation degrees may vary within the above-mentioned ranges depending on which basic linker components are used. The use of polyethylene glycols (PEG) in which both L1 and L2 are hydroxyl groups is particularly preferred. The mentioned linkers preferably have a molecular weight of 1-50 kDa.

Polyorganosiloxanes, which may be linear or branched, are used in the invention as active compounds ensuring the desired blood compatibility of the plastic surface. The use of poly(dialkyl siloxane) of the formula $R_3SiO[R_2SiO]_nSiR_3$ has proven to be advantageous, wherein the groups R may be the same or different, representing hydrogen atoms or alkyl groups having 1 to 8, preferably 1 to 4, more preferably 1 to 2 C-atoms. n is a natural number, which should be selected in such a way that the viscosity degree of the siloxane is between 10 and 25000, preferably between 500 and 5000 $mm^2/s$. The use of dimethyl polysiloxane (Dimeticon) is particularly preferred due to its known good physiological acceptability. In this case, in the aforementioned formula R is $CH_3$, n is preferably between 1 and 50, particularly preferred between 1 and 20.

The mentioned inhibitors of blood platelets or cell activation are linked with the above-mentioned linkers and subsequently contacted as linker-active substance conjugate with the plastic surface. Also in this case, the use of dimethyl polysiloxane is advantageous, since polyethylene glycol compounds of this composition are already commercially available, e.g. from Hüls having the product names MN 4221, MN 4217, MN 4205 and MN 4211.

After linking the activation inhibitor with the linker, the obtained conjugate is linked to the polymer surface. The linkage occurs upon mere contact of the linker-active agent conjugates with suitable polymer surfaces, without necessitating higher temperatures or the use of catalysts or other reaction accelerating reagents. It can be obtained e.g. by incubation of the polymer material in a preferably aqueous solution of the conjugates. The optimum concentration of the conjugates in the solution depends e.g. on the solubility of the used components and the surface coverage to be obtained. It is, however, frequently between 0.1 µg/ml and 100 mg/ml, preferably between 1 and 10 mg/ml. After an exposure time of a few minutes and optionally rinsing with a physiological sodium chloride or buffer solution, the siliconisation of the surface is finished.

The bond formed on the boundary layer produced is of excellent stability and cannot be detached in aqueous solutions by shifting the pH value within a range of from 2 to 13. The bond is also resistant to rinsing with salt solution of high ion strength (2n glycine, 2n urea). Thus, it can be considered irreversible under physiological conditions.

The binding density on the coated surface is already remarkably high as soon as it has been brought into contact with the conjugate made of linkers and active agents under standard conditions, e.g. at room temperature. A plastic material treated in advance in such a way is able to completely prevent the activation of cellular blood constituents, in particular of thrombocytes, but also the immobilisation of fibrinogen and other proteins on its surface. However, further tests revealed that by supplying exogenous energy, e.g. thermal energy, e.g. by treating in an autoclave (increased temperature, superheated steam), by increasing the pressure or by the influence of γ-rays in a ray sterilization apparatus, the coverage density and the binding strength could surprisingly be further increased considerably beyond the extent obtained under standard conditions.

Furthermore, it was revealed that even if the surfaces according to the invention are only partly covered by the conjugates made of ligands and active agents, they already exhibit the required blood-neutral surface without preventing the immobilisation of other active substances comprising ligands according to the outlined principle. Thus, at a coverage density of at most 50% of the maximum coverage that can be obtained under standard conditions, excellent blood compatibility of the treated surface is guaranteed. Depending on the structure of the siloxane used, however, optimum results can already be achieved at considerably lower coverage densities of about 10 to 20%. The coverage density can, e.g., be limited by using conjugate solutions having very low concentrations, thereby limiting the concentration of the coating reaction. This provides a biscompatible surface which is of importance in the in vivo use in whole blood and, nevertheless, is available for the presentation and/or removal of further conjugates made of linkers and active agents as disclosed in WO 98/46648. Thus, e.g., pegylated active agents can be removed from the blood without coagulation at the exposed surface. Proteins, nucleic acids, oligo- or polynucleotides, hormones, enzymes, antigens, antibodies, carbohydrates or other cellular signal substances and immunological messenger substances can, inter alia, be used as additional bioactive effective and recognition structures.

The boundary layers according to the invention can also contribute to considerable improvements in the compatibility of materials used in implantation medicine, since harmful interactions, e.g. unspecific inflammations, can be prevented even at the tissue and blood boundary layers. The fact that it is nevertheless simultaneously possible to have active agents linked to linkers act specifically on the bio-microenvironment opens completely new ways for the long-term use of such materials.

The resistance to blood or protein over long periods of use which is characteristic of the surfaces according to the invention is of importance not only as regards medical materials, but also as regards medical devices and instruments. The invention makes it possible to prevent the proteinisation of such devices, e.g. long-term catheters, which provides an ideal breeding ground for bacteria and, thus, promotes secondary infections. Thus, the boundary layer according to the present invention makes it possible to use suitable plastic materials which have been modified to be antibacterial or antimicrobial.

Apart from their complete compatibility with samples containing proteins, in particular blood samples or circulating whole blood, the modified plastic surfaces of the present invention are suitable for the presentation of immobilised active agents, but also for the immobilisation and/or removal of linker-coupled active substances or recognition structures. Thus, active agents can immediately be introduced into the bloodstream or removed therefrom after having been coupled to a corresponding linker. Thus, the surfaces according to the invention open up numerous new indications and fields of application in therapeutics as well as in diagnostics, but also in related fields, such as diethetics.

The following examples illustrate the effectiveness of the surface coatings according to the invention.

In these examples, monodisperse polymethyl methacrylate particles having a size of 5.9 to 6.1 µm (Microparticles GmbH Berlin) as well as commercial dialysers of the series BK 05 of Toray Industries, Tokyo (surface area 0.5 m$^2$) and experimental microdialysers prepared therefrom and having a surface area of 100 m$^2$ are used.

TEST EXAMPLE 1

50 µl of 5% polymethyl methacrylate particle solution (particle diameter 5.9-6.1 µm) are blended with PEG dimethyl polysiloxane (MN 4205) in a concentration of 1 µg/ml for 10 min in a roller type agitator. Subsequently, the particles are sedimented by short-time centrifugation at 1000 g for 3 min and the supernatant is removed. The particles are then taken up in 1 ml tyrode solution, agitated for a short time and after sedimentation once again washed with tyrode and stored for further use in tyrode solution. R-hirudin in a concentration of 300 µg/ml is blended with 10 ml whole blood in a test tube. Freshly collected human blood is blended with sedimented particles which had in advance been blended with PEG dimethyl polysiloxane. After 15, 20, 30 and 40 min, the samples which have been agitated well in a roller type mixer are transferred into a CellDyn 2000 analyzer for platelet measurement and the number of platelets is determined. Particles which had not been coated with PEG dimethyl polysiloxane are used for comparison. It could be shown that a large number of the circulating blood platelets are immobilised in the suspension containing uncoated particles. Within the first 10 minutes, a sharp decrease in the number of platelets occurs in the sample, which, after this depression in the number of cells has been reached, increases only slightly due to opposite disaggregation processes. Nevertheless, the majority of the platelets in the blood sample remains adhered to the polymer surface (>90%). As compared therewith, in the suspension containing particles which had been coated with dimethyl polysiloxane, these changes in the number of platelets cannot be detected. During the whole duration of the test the number of platelets could be proven to be equivalent to the original values.

TEST EXAMPLE 2

Figure 1:
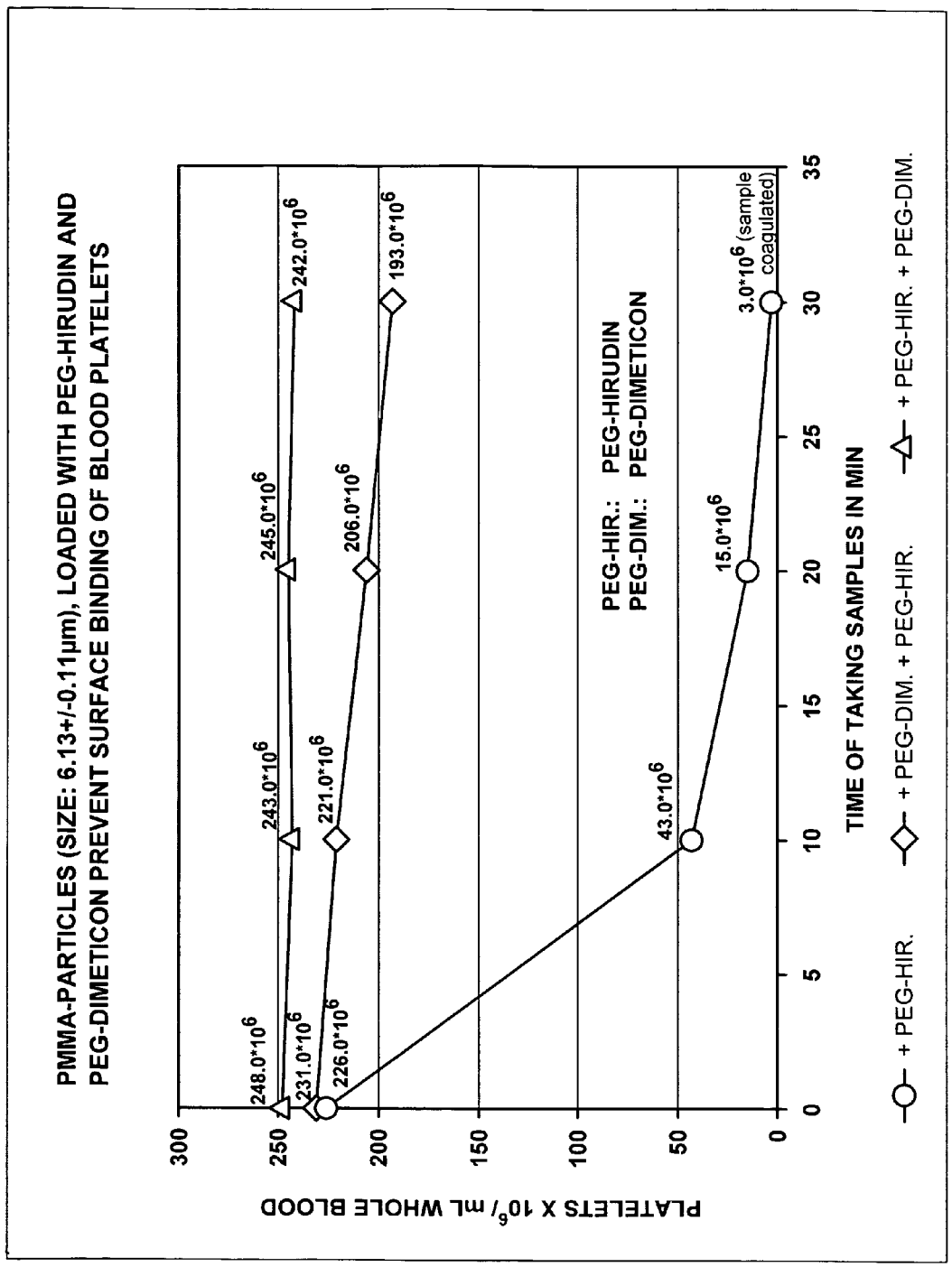
FIG. 1 is a graph of experimental results for PMMA-particles loaded with PEG-Hirudin and PEG-Dimeticon in preventing surface binding of blood platelets.
Figure 2:
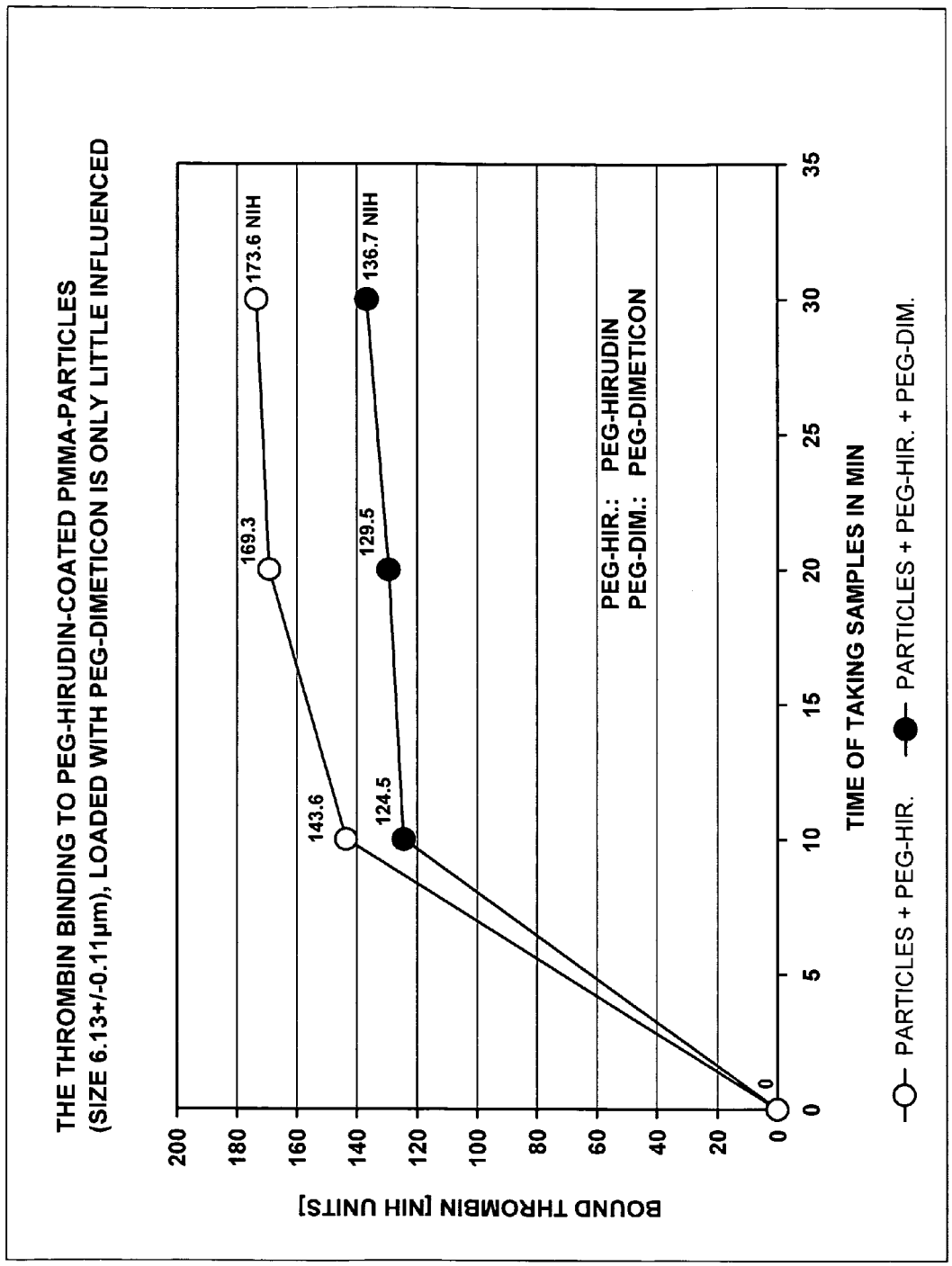
FIG. 2 is a graph of experimental results for thrombin binding to PEG-Hirudin-coated PMMA-particles, and to the particles also loaded with PEG-Dimeticon.

Another series of tests were carried out under conditions identical to those of example 1, except that the blood had been anti-coagulated with PEG hirudin. FIG. 1 shows the corresponding results. In the particle suspension without PEG dimethyl polysiloxane coating, almost all of the blood platelets adhere to the particles within 10 to 15 min upon addition to PEG hirudin anti-coagulated blood. Within 30 min the sample coagulates as the PEG hirudin is completely linked to the particles. By treating the particles in advance with PEG dimethyl polysiloxane, the platelet decrease can be stopped completely, but even in this experiment the well blended sample coagulates within about 40 min. When measuring the hirudin concentration in the samples it becomes evident that, in contrast to the samples which had been treated with r-hirudin, in which a constant hirudin blood concentration of 25 to 30 mg/ml r-hirudin can be detected during the whole duration of the test over 60 min, a continuous decrease in the PEG hirudin concentration can be detected in the PEG hirudin samples. After 30 min the PEG hirudin content has decreased to 3 µg/ml, after 40 min the samples contain no PEG hirudin at all. It is clearly evident from the test presented above that the adsorption of platelets is prevented by treating the microparticles in advance with PEG dimethyl polysiloxane in a concentration within the range between 0.1 and 1 µg/ml without impairing the binding of pegylated hirudin to the particle surface. When compared to in vitro tests in which PEG hirudin is added to the microparticle solutions, a decrease in the PEG hirudin binding capacity by advance treatment with PEG dimethyl polysiloxane cannot be detected. Furthermore, it was examined whether the thrombin bond to the particles which, after they had been treated in advance with PEG dimethyl siloxane, formed an additional bond with PEG hirudin had remained intact. In this context, FIG. 2 illustrates a test example. It could be shown without doubt that the thrombin affinity remained almost completely intact.

TEST EXAMPLE 3

Experimental PMMA dialysers having a surface area of 100 cm$^2$ are rinsed with dimethyl polysiloxane solutions in a concentration of 1 µg/ml by means of an in vitro circulation unit for 10 min and subsequently washed with tyrode solution. Subsequently, the microcapillary dialysers are treated with PEG hirudin-anti-coagulated whole blood (50 µg/ml) in a recirculation apparatus. In this test arrangement, it can also be shown without doubt that in spite of the binding of PEG hirudin to the capillary surfaces there is no decrease in the number of platelets. Although the majority of the PEG hirudin is immobilised on the PMMA surface of the dialysers, the systems can be recirculated for more than 30 min without any substantial increase in pressure.

The invention claimed is:

1. Blood-compatible surface comprising a polymer surface and a plurality of conjugates made of linkers and active agents immobilised thereon, wherein said polymer surface contains the same or different structural units that carry carbonyl groups, said linkers contain a structural element that is able to form a hydrogen bridge bond and wherein a polyorganosiloxane acting as the active agent is linked to the linkers.

2. The surface as claimed in claim 1, wherein said polymer surface contains a plurality of structural units which are the same or different and are selected from the group consisting of polyalkyl methylacrylate, polyvinyl acetate polycyclohexyl methacrylate and/or polyphenyl methacrylate units.

3. The surface as claimed in claim 1, wherein said linkers are the same or different and are selected from the group consisting of polyalkylene glycol, polyalkylene imine, polyalkylene amine, polyalkylene sulfide and polyoxacilline.

4. The surface as claimed in any one of claims 1, wherein dimethyl polysiloxane is used as the active agent.

5. The surface as claimed in claim 1, wherein the surface has a coverage density of conjugates made of linkers and active agents that is at most 50% of the maximum coverage that can be obtained under standard conditions.

6. The surface as claimed in claim 1, comprising additional conjugates made of linkers and active agents, said active agents further providing the surface with bioactivity in addition to blood compatibility.

7. Plastic article comprising a blood-compatible surface as claimed in claim 1.

8. Medical device or instrument comprising a blood-compatible surface as claimed in claim 1.

9. The device or instrument as claimed in claim 8 in the form of a sample container, a blood tube, a catheter, a dialyser or components thereof.

10. Stent or implantation material comprising a blood-compatible surface as claimed in claim 1.

11. Process for the preparation of a blood-compatible surface as claimed in claim 1 comprising contacting the polymer surface with said conjugates made of linkers and active agents.

12. The process as claimed in claim 11, wherein said polymer surface is incubated in a solution of said conjugates made of linkers and active agents.

13. The process as claimed in claim 11, wherein the surface has a coverage density of conjugates made of linkers and active agents that is at most 50% of the maximum coverage that can be obtained under standard conditions.

14. The process as claimed in claim 11, additionally comprising the supply of erogenous energy during or after contacting the polymer surface with said conjugates to increase the coverage density as compared to a like process without the supply of exogenous energy.

15. The process as claimed in claim 14, wherein energy is supplied by high pressures, thermally or via x-rays.

16. Diagnostic method comprising contacting a blood sample with a surface as claimed in claim 1.

17. A method of storage of human blood outside the human body, comprising a) providing a plastic article of claim 7, and
  b) contacting human blood with the plastic article while storing human the blood.

18. A method of sport of human blood outside the human body, comprising
  a) providing a plastic article of claim 7, and
  b) contacting human blood with the plastic article while transporting human the blood.

19. A method of testing of human blood outside the human body, comprising
  a) providing a plastic article of claim 7, and
  b) contacting human blood with the plastic article while testing the human blood.

* * * * *